United States Patent
Lali et al.

(10) Patent No.: US 9,975,866 B2
(45) Date of Patent: May 22, 2018

(54) PROCESS FOR SYNTHESIS OF FURAN DERIVATIVE USING AN ACID CATALYST AND PREPARATION THEREOF

(71) Applicants: DEPARTMENT OF BIOTECHNOLOGY, MINISTRY OF SCIENCE AND TECHNOLOGY, GOVERNMENT OF INDIA, New Delhi (IN); INSTITUTE OF CHEMICAL TECHNOLOGY, Mumbai (IN)

(72) Inventors: Arvind Mallinath Lali, Mumbai (IN); Hitesh Suresh Pawar, Mumbai (IN)

(73) Assignees: DEPARTMENT OF BIOTECHNOLOGY. MINISTRY OF SCIENCE AND TECHNOLOGY, GOVERNMENT OF INDIA, New Delhi (IN); INSTITUTE OF CHEMICAL TECHNOLOGY, Mumbai (IN)

( * ) Notice: Subject to any disclaimer, the term of this patent is extended or adjusted under 35 U.S.C. 154(b) by 0 days. days.

(21) Appl. No.: 15/038,416

(22) PCT Filed: Nov. 21, 2014

(86) PCT No.: PCT/IB2014/002537
§ 371 (c)(1),
(2) Date: May 20, 2016

(87) PCT Pub. No.: WO2015/075540
PCT Pub. Date: May 28, 2015

(65) Prior Publication Data
US 2016/0289203 A1    Oct. 6, 2016

(30) Foreign Application Priority Data
Nov. 21, 2013    (IN) .......................... 3664/MUM/2013

(51) Int. Cl.
| | | |
|---|---|---|
| C07D 307/50 | (2006.01) |
| B01J 31/10 | (2006.01) |
| C07D 307/46 | (2006.01) |
| B01J 31/06 | (2006.01) |
| B01J 37/00 | (2006.01) |
| B01J 37/04 | (2006.01) |

(52) U.S. Cl.
CPC ............ *C07D 307/46* (2013.01); *B01J 31/06* (2013.01); *B01J 37/009* (2013.01); *B01J 37/04* (2013.01); *C07D 307/50* (2013.01); *B01J 2231/4288* (2013.01); *B01J 2531/004* (2013.01)

(58) Field of Classification Search
CPC .................. C07D 307/50; C07D 307/46; B01J 2231/4288
See application file for complete search history.

(56) References Cited

U.S. PATENT DOCUMENTS

| 7,579,489 B2 | 8/2009 | Sanborn | |
|---|---|---|---|
| 2009/0156841 A1 | 6/2009 | Sanborn et al. | |
| 2010/0261800 A1* | 10/2010 | Daniel | ................. C07C 29/149 518/702 |
| 2014/0357878 A1* | 12/2014 | Zhang | ................. C07D 307/48 549/488 |

FOREIGN PATENT DOCUMENTS

| EP | 2233476 A1 | 9/2010 |
|---|---|---|
| WO | WO 2009-076627 A2 | 6/2009 |
| WO | WO 2011-124639 A1 | 10/2011 |
| WO | WO 2012-015616 A1 | 2/2012 |
| WO | WO 2013043131 * | 3/2013 |
| WO | WO 2014-180979 A1 | 11/2014 |

OTHER PUBLICATIONS

Aellig, et al., "Continuous d-Fructose Dehydration to 5-Hydroxymethylfurfural Under Mild Conditions," *ChemSusChem*, 5, pp. 1737-1742, 2012.
De, et al., "Microwave assisted conversion of carbohydrates and biopolymers to 5-hydroxymethylfurfural with aluminium chloride catalyst in water," *Green Chemistry*, 13, pp. 2859-2868, 2011.
Dutta et al., "Microwave assisted rapid conversion of carbohydrates into 5-hydroxymethylfurfural catalyzed by mesoporous TiO2 nanoparticles", *Applied Catalysis A: General 409-410*, pp. 133-139, 2011.
Hansen et al., "Efficient microwave-assisted synthesis of 5-hydroxymethylfurfural from concentrated aqueous fructose," *Carbohydrate Research*, 34, pp. 2568-2572, 2009.
Lai, et al., "The Production of 5-Hydroxymethylfurfural from Fructose in Isopropyl Alcohol: A Green and Efficient System," *ChemSusChem*, 4, pp. 1745-1748, 2011.
Qi, et al., "Catalytic dehydration of fructose into 5-hydroxymethylfurfural by ion-exchange resin in mixed- aqueous system by microwave heating", *Green Chemistry*, 10, pp. 799-805, 2008.
Qi, et al., "Selective Conversion of D-Fructose to 5-Hydroxymethylfurfural by Ion-Exchange Resin in Acetone/ Dimethyl sulfoxide Solvent Mixtures," *Industrial & Engineering Chemistry Research*, 47, pp. 9234-9239, 2008.

(Continued)

*Primary Examiner* — Jeffrey C Mullis
(74) *Attorney, Agent, or Firm* — Knobbe, Martens, Olson & Bear, LLP

(57) ABSTRACT

In accordance with the present subject matter, there is provided a process for preparing a furan derivative, the process comprising the steps of contacting a sugar with a monophasic organic solvent to obtain a reaction mixture; and subjecting the reaction mixture to a temperature in the range from 100° C. to 180° C., in presence of an acid catalyst, for a time period in the range of 0.5 min to 4.0 h to obtain at least 70% conversion of the sugar to a single furan derivative, wherein the acid catalyst is selected from the group consisting of homogenous acid catalyst, heterogenous solid acid catalyst, and combinations thereof. There is also provided a process for preparation of a heterogenous solid acid catalyst.

10 Claims, No Drawings

(56) References Cited

OTHER PUBLICATIONS

Shimizu, et al., "Enhanced production of hydroxymethylfurfural from fructose with solid acid catalysts by simple water removal methods," Catalysis Communications, 10, pp. 1849-1853, 2009.

* cited by examiner

PROCESS FOR SYNTHESIS OF FURAN DERIVATIVE USING AN ACID CATALYST AND PREPARATION THEREOF

PRIORITY AND CROSS REFERENCE TO RELATED APPLICATIONS

This application is the U.S. National Stage Application under 35 U.S.C. § 371 of International Application No. PCT/IB2014/002537, filed Nov. 21, 2014, designating the U.S. and published in English as WO 2015/075540 A1 on May 28, 2015, which claims the benefit of Indian Patent Application No. IN 3664/MUM/2013, filed Nov. 21, 2013.

TECHNICAL FIELD

The subject matter herein in general relates to a process for synthesis of furan derivative using an acid catalyst in monophasic organic solvent. The subject matter further relates to acid catalysts and preparation thereof.

BACKGROUND

Furan derivatives such as 5-methyl furfural and 5-methyl furfural alcohol as well as hydroxymethyl furfural and furfural are products of saccharide dehydration with high industrial value. The 5-hydroxy methyl furfural (5-HMF) is a multipurpose and multi functional organic molecule having wide range of application in various sectors of synthetic organic chemistry e.g. bulk chemicals, fine chemicals, pharmaceuticals, agrochemicals, polymer, and chemical intermediates etc. The structure of 5-HMF is shown below:

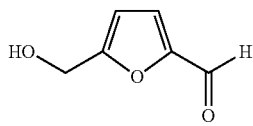

5-Hydroxy methyl furfural

The process for 5-HMF synthesis is of great interest in chemical industries due to its potential for production of industrially important bio-based chemicals such as furan 2,5-dicarboxylic acid (FDCA) which is required for production of bio-based polymer, chemicals and pharmaceuticals etc. Furans 2,5-dicarboxylic acid derived polymers have potential replacements for the petro-based terephthalic acid polymer. Thus, the huge replacement of petro based polymer by bio-based polymer provide great platform of green chemistry in the sector of polymer industry. But the key role for these replacement is synthesis of 5-HMF and therefore 5-HMF synthesis occupy nutshell position for synthesis of bio-based products.

The synthetic chemistry of 5-HMF begins with hexose sugars, glucose and fructose, more specifically from fructose via acid catalyzed cyclodehydration reaction. Since the synthetic chemistry applications for 5-HMF production is directed towards the development of acid catalysis. A number of acid catalysts like mineral acids, inorganic acids, and solid adds have been employed for this purpose. But the synthetic process for production of 5-HMF by acid catalysis suffers from many technical problems in terms of yield, selectivity, process feasibility and process economics. Due to complex chemical properties between reaction substrate, catalyst used for dehydration and reaction products separation, number of issues are raised during synthesis of 5-HMF.

Another important factor that affects 5-HMF synthesis is the type of catalyst used for dehydration reaction. Various types of organic, inorganic and mineral acids have been employed as in situ catalysts for 5-HMF synthesis. But most of these processes suffer from handling problems due to corrosive nature of mineral acids as well as difficult catalyst separation protocols from reaction mixture with subsequent recycling of the catalyst.

Therefore heterogeneous acid catalysis as well as various solid acid catalysts such as zeolites, silica, and amberlyst resins have been explored and investigated as a possible alternative. Ken-ichi Shimizu and co-workers reported use of heteropoly acid, zeolites, and acidic resin (*Catalysis Communications*, 2009, 10, 1849-1853) with DMSO as solvent. Though the use of heterogeneous catalysis resulted in higher yield, high boiling point of solvent rendered separation of the product difficult.

Yugen zhang report (*ChemSusChem*, 2011, 12, 1745-1748) disclosed the synthesis of 5-HMF in isopropyl alcohol with aqueous HCl as a catalyst. However, the use of halogenated corrosive HCl as a catalyst in aqueous condition resulted in product separation problem as well as recovery of catalyst with difficulty in handling during large scale production.

US2007757461 discloses use of mineral acid, zeolites, silica-, silica-alumina, and titania-based supports functionalized by acid groups, cation exchange resin, Lewis acid, heteropolyacid, in biphasic reactor, having aqueous and organic phase of 1-butanol, DCM, MIBK, 2-butanol, and mixtures thereof. However, the invention also employs modifier such as DMSO, DMF, N-methyl pyrrolidinone (NMP), which are difficult to separate and non eco-friendly.

Similarly patent documents WO2009/076627, US2009/0156841, U.S. Pat. No. 7,579,489, EP2233476, and Lve et. al (*ChemSusChem*, 2012, 5, 1737-1742) disclose the use of a heterogeneous catalyst, amberlyst-35 resin, in high boiling solvents like DMF, N-methylpyrrolidinone (NMP) with yield figure less than 80%. The solvents used are non green and require high energy to separate them from reaction mass.

Typically aqueous biphasic solvents and ionic liquids are used for the synthesis of 5-HMF in presence of acid catalyst. However, due to higher solubility of 5-HMF in water, procedures become complicated and require large amounts of organic solvents for extraction. This leads to substantial increase in the process cost and unit operation for the bulk production of 5-HMF. This necessitates the optimization of solvent and catalytic systems that would be cost effective as well as provide ease of process operation.

WO2011124639 recites claims to the use of mineral and Lewis acid catalyst such as aqueous HCl, $AlCl_3$ respectively by using salt, NaCl, LiCl, LiBr, $LiNO_3$, KCl, KBr, $KNO_3$, $FeCl_3$, etc. in biphasic organic solvent, wherein the biphasic organic solvent consisted of mixture of water and methyl isobutyl ketone (MIBK). However, the disclosed process of the invention resulted in low yield (52%) and selectivity (less than 65%). The process also employs halogenated catalyst and salts which cause corrosion problems as well as environmental hazards.

Microwave assisted reaction for synthesis of 5-HMF has gained significance as it leads to reduction in reaction time, increases selectivity and also results in reduction of energy consumptions. Thomas S. Hansen and co-workers (*Carbohydrate Research*, 2009, 344, 2568-2572) reported microwave assisted synthesis of 5-HMF by using Aq. HCl catalyst at 200° C. temp with only 52% HMF yield. Xinhua Qi, and co-workers (*Ind. Eng. Chem. Res.* 2008, 47, 9234-9239) reported HMF synthesis by employing strong acidic cation-exchange resin catalyst and a mixed organic solvent system comprising acetone and DMSO in ratio of 70:30 w/w under microwave heating condition. The reaction resulted in 80% yield with a reaction time period of 10-30 min.

Sudipta De and co-workers (*Green Chem,* 2011, 13, 2859) report microwave assisted synthesis of 5-HMF by using Lewis acid catalyst $AlCl_3$ with 21.4-60.6% yields in solvent DMSO and biphasic system, water—MIBK. Xinhua Qi and co-workers (Green Chem., 2008, 10, 799-805) employed microwave assisted heating for HMF synthesis in acetone-water mixtures in the presence of a cation exchange resin catalyst with yields of 5-HMF as high as 73.4%, with 94% conversion rate at 150° C. Sakita Dutta and co-workers (*Applied Catalysis A* vol. 409-410, 133-139), carried out microwave assisted 5-HMF synthesis by using mesoporous $TiO_2$ nanoparticals in solvents DMSO and NMP.

WO2012/015616 A1 claims for microwave assisted synthesis of 5-HMF by using catalyst amberlyst and $H_2SO_4$ in 5-30 min reaction time with 0-69.47% yield by using DMSO solvent. These methods of the microwave assisted synthesis for 5-HMF also reflect earlier predicaments of lower yield, selectivity, use of non-green solvent systems and higher cost economics that affect scaling up of the processes adversely.

WO2014180979 discloses a process for the synthesis of 5-hydroxymethyl furfural (HMF) from saccharides. In particular it discloses a process for the dehydration of monosaccharides having 6 carbon atoms (hexoses), disaccharides, oligosaccharides and polysaccharides deriving therefrom to yield highly pure 5-hydroxymethyl furfural (HMF) in high yield.

The methods of prior art disclose the use of various catalyst and solvent systems for synthesis of 5-HMF through microwave assisted as well as conventional means. Evidently, these methods are associated with issues pertaining to higher cost economics, reaction feasibility, longer reaction time, catalysts and product separation, low catalyst activity, low selectivity & yield, and use of non-green solvents that pose environmental hazards.

Accordingly, there has been a need in the prior art for a process for synthesis of 5-HMF, wherein the process results in higher selectivity and yield; has a higher conversion rate with enhanced catalytic stability, has ease of product separation and most importantly has the advantage of recycling the catalyst with 100% recovery.

SUMMARY

The present disclosure relates to a process for preparing a furan derivative, the process comprising the steps of: a) contacting a sugar with a monophasic organic solvent to obtain a reaction mixture; and b) subjecting the reaction mixture to a temperature in the range from 100° C. to 180° C., in presence of an acid catalyst, for a time period in the range of 0.5 min to 4.0 h to obtain at least 70% conversion of the sugar to a single furan derivative, wherein the acid catalyst is selected from the group consisting of homogenous acid catalyst, heterogeneous solid acid catalyst, and combinations thereof.

The present disclosure also relates to a process for preparing a heterogeneous solid acid catalyst, the process comprising the steps of: contacting a sulfonating agent with a polymer in presence of an organic solvent to obtain a reaction suspension; agitating the reaction suspension at a temperature in the range of 35° C. to 100° C. for a time period in the range of 30 min to 4 hrs to obtain a suspension of heterogeneous acid catalyst; and isolating the suspension of heterogeneous acid catalyst to obtain a heterogeneous solid acid catalyst.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term "$DIC_AT$" used herein refers to the solid acid catalyst disclosed in the present invention and developed at DBT-ICT Centre for Energy Biosciences, Institute of Chemical Technology. Various solid acid catalysts prepared by using different polymeric support and disclosed in the present invention, and further disclosed in the present invention are:

$DIC_AT$-1:—DBT-ICT-CEB Catalyst prepared by using polyvinyl alcohol $DIC_AT$-2:—DBT-ICT-CEB Catalyst prepared by using cellulose $DIC_AT$-3:—DBT-ICT-CEB Catalyst prepared by using hydroxy acrylate polymer The term "saccharides" used herein refers to sugars having composition according to formula $(CH_2O)n$ consisting of monosaccharide, disaccharides and/or polysaccharides. The word "sugars" has been interchangeably used in this disclosure with the word "saccharides".

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a temperature range of about 70° C. to about 180° C. should be interpreted to include not only the explicitly recited limits of about 70° C. to about 180° C., but also to include sub-ranges, such as 90° C. to 110° C., 120° C. to 160° C., and so forth, as well as individual amounts, including fractional amounts, within the specified ranges, such as 82° C., 121.6° C., and 168.3° C., for example.

As discussed above, methods of synthesis of 5-hydroxy methyl furfural (5-HMF) using various catalyst and solvents through microwave assisted method and conventional methods as disclosed in the prior arts have several drawbacks such as longer reaction time, higher cost, catalyst and product separation, low catalyst activity, and low yield. The present disclosure is directed to a process for synthesis of a furan derivative, more particularly 5-hydroxy methyl furfural (5-HMF), from sugars with a short time microwave assisted or conventional heating reaction, by using homogeneous or heterogeneous-solid acid catalyst. The use of the acid catalyst in monophasic organic solvent system for the synthesis of 5-HMF provides excellent catalytic activity, selectivity, conversion, rate of production and yield of product. Also, the use of a heterogeneous-solid acid catalyst, $DIC_4T$, in the present invention provides the convenience of a simple process for separating the catalyst from the reaction mixture. The reaction products and catalyst are easily separated from reaction mixture by conventional methods such as simple solvent distillation and filtration procedures.

The process for preparing a furan derivative as disclosed herein, comprises the steps of a) contacting a sugar with a monophasic organic solvent to obtain a reaction mixture; and b) subjecting the reaction mixture to a temperature in the range from 100° C. to 180° C., in presence of an acid catalyst, for a time period in the range of 0.5 min to 4.0 h to obtain at least 70% conversion of the sugar to a single furan derivative, wherein the acid catalyst is selected from the group consisting of homogenous acid catalyst, heterogeneous solid acid catalyst, and combinations thereof.

The present disclosure further relates to a process for preparing a heterogeneous solid acid catalyst, the process comprising the steps of: a) contacting a sulfonating agent with a polymer in presence of an organic solvent to obtain a reaction suspension; b) agitating the reaction suspension at a temperature in the range of 35° C. to 100° C. for a time period in the range of 30 min to 4 hrs to obtain a suspension of heterogeneous acid catalyst; and c) isolating the suspension of heterogeneous acid catalyst to obtain a heterogeneous solid acid catalyst.

In one implementation, the furan derivative prepared by the disclosed process is 5-hydroxy methyl furfural (5-HMF).

Saccharides are used as substrates for synthesis of furan derivatives. In one implementation, saccharide sources used for the disclosed process include, but are not limited to hexose and pentose sugars, polysaccharides comprising at least one hexose, corn syrup, high fructose corn syrup, cane sugar molasses, fructose, fructose syrup, crystalline fructose, crude fructose; purified fructose, high fructose concentration, fructose syrup or combinations thereof. In one implementation, the substrate is a hexose sugar. In one implementation, the sugar is selected from the group consisting of glucose, fructose, sucrose, and combinations thereof. In another implementation, the sugar is fructose. In one application, the form of fructose is anhydrous. In one implementation, the sugar is in amorphous form. In one implementation, the sugar is in crystalline form.

The solvent as used in the process disclosed herein is a monophasic organic solvent. In one implementation, the solvent is selected from the group consisting of alcohols with the formula R—OH, N, N-Dimethyl formamide, Dimethyl sulfoxide, esters, and 1,4-dioxane. In one implementation, the solvent is an alcohol with the formula R—OH, wherein R ranges from $C_1$ to $C_{15}$, more preferably $C_1$ to $C_4$. In one implementation, the $C_1$ to $C_4$ alcohol is selected from the group consisting of methanol, ethanol, n-propanol, isopropanol, sec-butanol, tert-butanol, and combinations thereof. In another implementation, the $C_1$ to $C_4$ alcohol is isopropanol. In one implementation, the monophasic organic solvent has a boiling point less than 100° C.

The reaction mixture for preparing a furan derivative comprises a sugar and a low boiling point organic solvent. In one implementation, the concentration of sugar in the reaction mixture is in the range of 1-50% (w/v), preferably 1-10% (w/v). In one implementation, the water content in the reaction mixture is in the range of 0 to 20%, preferably 0 to 6% w/w.

In one implementation, the reaction is carried out at a temperature in the range of 100-180° C. In one implementation, contacting the reaction mixture with microwave radiation to bring it to a temperature in the range of 100° C. to 180° C. for a desired time is sufficient to convert at least 70% of the reactant into the desired product. In another implementation, contacting the reaction mixture with microwave radiation to bring it to a temperature in the range of 100° C. to 180° C. for a desired time is sufficient to convert at least 90% of the reactant into the desired product.

In one implementation, the reaction is carried out at a temperature in the range of 100-180° C. In one implementation, contacting the reaction mixture with a conventional heater bringing it to a temperature in the range of 100° C. to 180° C. for a desired time is sufficient to convert at least 70% of the reactant into the desired product. In another implementation, contacting the reaction mixture a conventional heater bringing it to a temperature in the range of 100° C. to 180° C. for a desired time is sufficient to convert at least 90% of the reactant into the desired product.

In an implementation, process for synthesis of 5-HMF is carried out in a microwave reactor, wherein the temperature is in the range of 100-180° C. In another implementation, the preferred temperature is in the range of 110-150° C. under microwave heating condition. In one implementation, the process provides the use of microwave reactor with frequency of 2.45 GHz, and power ranging between 10-400 watts. In one implementation, the reaction mixture is stirred at the rotational speed ranging between 200-800 rpm. In another implementation, the reaction mixture is stirred at the rotational speed ranging between 400-650 rpm. In one implementation, the reaction is carried under microwave heating conditions for 30-300 seconds. In another implementation, the reaction is carried under microwave heating conditions for 30-120 seconds.

In one implementation, the process for synthesis of 5-HMF is carried out by means of conventional heating under pressure in the range of 5-50 bar. In another implementation, conventional heating is done under pressure in the range of 5-30 bar. In one implementation, the reaction mixture is heated to a temperature in the range of 100-180° C. In another implementation, the reaction mixture is heated to a temperature in the range of 100-150° C. The temperature was maintained by proportional-integral-derivative (PID) heating temperature controller. In one implementation, reaction time under conventional heating is in the range of 0.5-5 hrs. In one implementation, reaction time under conventional heating is in the range of 0.5-4 hrs. In one implementation, reaction time under conventional, heating is in the range of 0.5-3 hrs. In one implementation, the agitation of reaction mixture is carried out by four pitch bladed impeller at a rotational speed in the range of 100-800 rpm.

In one implementation, conversion of the sugar by the process disclosed herein is in the range of 45-100%. In another implementation, conversion of the sugar by the process disclosed herein is in the range of 95-100%.

In one implementation, the yield of furan derivative by the process disclosed herein is in the range of 10-95%. In another implementation, the yield of furan derivative by the process disclosed herein is in the range of 80-95%.

In one implementation, the process is carried in a batch mode reactor. In one implementation, the process is carried out in a continuous reactor. In one implementation, the process is carried out in the fixed bed reactor.

The process for preparation of a furan derivative from a sugar is carried out in presence of an acid catalyst. In one implementation, the acid catalyst is used in an amount in the range of 0.01 to 5 g/cc of the reaction mixture. In another implementation, the acid catalyst is used in an amount in the range of 0.1 to 1.0 g/cc of the reaction mixture.

Following conversion of sugar to a furan derivative, the reaction mixture is cooled and the catalyst is separated by filtration and reused for next reaction. In one implementation, recycling of catalyst is performed up to 20 times without addition of fresh catalyst and without regeneration. In another implementation, recycling of catalyst is performed more than 20 times without addition of fresh catalyst and without regeneration. In another implementation, recycling of catalyst is performed up to 5 times without addition of fresh catalyst and without regeneration.

In one implementation, the acid catalyst is a homogenous acid catalyst. In one implementation, the homogenous acid catalyst is an aliphatic sulfonic acid. In one implementation, the homogenous acid catalyst is an aromatic sulfonic acid. In one implementation, the aromatic sulfonic acid is selected from the group consisting of naphthalene sulfonic acids, dimethyl aniline sulfonic acid, para-toluene sulfonic acid (p-TSA), ortho/meta-toluene sulfonic acid (o/m-TSA), and combinations thereof. In another implementation, the aromatic sulfonic acid is para-toluene sulfonic acid (p-TSA).

In one implementation, the acid catalyst is a heterogenous solid acid catalyst. In one implementation, the heterogenous solid acid catalyst is a hydrophilic sulfonated solid porous matrix. In one implementation, the heterogenous solid acid catalyst is $DIC_AT$ acid catalyst.

In one implementation, there is provided a process for preparing a heterogenous solid acid catalyst. The process for preparing a heterogenous solid acid catalyst comprises the steps of: a) contacting a sulfonating agent with a polymer in presence of an organic solvent to obtain a reaction suspension; b) agitating the reaction suspension at a temperature in the range of 35° C. to 100° C. for a time period in the range of 30 min to 4 hrs to obtain a suspension of heterogeneous acid catalyst; and c) isolating the suspension of heterogeneous acid catalyst to obtain a heterogeneous solid acid catalyst.

In one implementation, the sulfonating agent is selected from the group consisting of chlorosulfonic acid, sulphuric acid, sulfur trioxide, and combinations thereof. In one implementation, the sulfonating agent is chlorosulfonic acid.

In one implementation, the heterogenous solid acid catalyst is composed of a hydrophilic functionalized polymer. In one implementation, the functionalized polymer has a surface area in the range of 5-200 $m^2/g$. In another implementation, the functionalized polymer has a surface area in the range of 5-50 $m^2/g$, pore size in the range of 2-50 nm, acidity in the range of 0.5-10 mmol/g, pore volume in the range of 0.022-2.0 cc/g. In one implementation, the molecular weight of the polymer is in the range of 3-23 kDa, particle size is in the range of 10-300 μm, and hydroxy value is in the range of 1 to 20 mg/g. In one implementation, the polymer is a homolinear polymer. In one implementation, the polymer is a crosslinked polymer. In one implementation, the polymer used is in crystalline form. In one implementation, the polymer used is in amorphous form. In one implementation, the polymer is in the form of spherical beads.

In one implementation, the polymer comprises hydroxy functional group. In one implementation, the polymer comprises amine functional group. In one implementation, the polymer is selected from the group consisting of cellulose, polyvinyl alcohol, polyhydroxyethylmethacrylate, polyhydroxymethylmethacrylate polyethylene glycol, polypropylene glycol, silica, alumina, polyethylene amine, polyamide, and polyallylamine. In another implementation, the polymer is selected from the group consisting of cellulose, polyvinyl alcohol, polyhydroxyethylmethacrylate, and polyhydroxymethylmethacrylate.

In one implementation, sulfonic acid derivatization of polymeric surfaces to obtain a heterogenous solid acid catalyst is done in presence of an organic solvent. In one implementation, the organic solvent is a non nucleophilic solvent. In one implementation, the organic solvent is selected from the group consisting of methylene dichloride, chloroform, carbon-tetrachloride, ethylene dichloride, propylene dichloride, and combinations thereof.

In one implementation, the heterogeneous solid acid catalyst as prepared by the process disclosed herein can also be used for various acid catalyzed organic transformation such as hydrolysis, elimination, addition, substitution, condensation, esterification, protection, deprotection, rearrangement, and ring opening.

In one implementation, there is disclosed a process for preparing 5-HMF, the process comprising the steps of: a) contacting fructose with isopropanol to obtain a reaction mixture; and b) subjecting the reaction mixture to a temperature of 120° C., in presence of an acid catalyst, for a time period of 2.0 min to obtain at least 70% conversion of fructose to 5-HMF, wherein the acid catalyst is PTSA.

In one implementation, there is disclosed a process for preparing 5-HMF, the process comprising the steps of: a) contacting fructose with isopropanol to obtain a reaction mixture; and b) subjecting the reaction mixture to a temperature of 130° C., in presence of an acid catalyst, for a time period in the range of 2.0 min to obtain at least 70% conversion of fructose to 5-HMF, wherein the acid catalyst is $DIC_AT$.

The disclosure is further illustrated with the following schemes:

Scheme 1. The reaction for 5-HMF synthesis from fructose is as follows

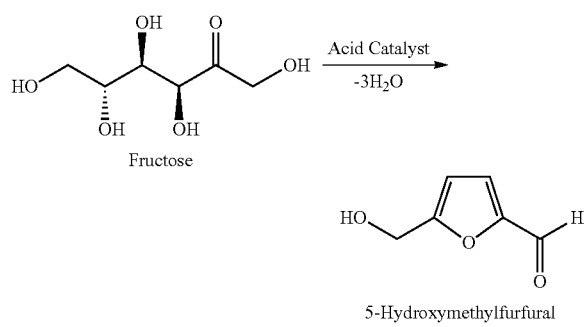

EXAMPLES

The disclosure will now be illustrated with working examples, which is intended to illustrate the working of disclosure and not intended to take restrictively to imply any limitations on the scope of the present disclosure. Other examples are also possible which are within the scope of the present disclosure.

Example 1

The experiment is carried out in batch mode operation under microwave heating at a frequency of 2.45 GHz. 1 gm of crystalline fructose was added to 8 ml isopropyl alcohol in a 20 ml sealed glass tube with magnetic stirrer; and stirred for 5 minute at room temperature to obtain a reaction suspension. 0.1 gm/cc of acid catalyst (as provided in Table 1) was added to this reaction suspension under continuous stirring. The resulting reaction mixture was heated to 120° C. under stirring for 120 seconds by subjecting to microwave radiation. After 120 seconds, the reaction mass was cooled to room temperature. The HPLC analysis of the sample was obtained which demonstrates 84-94% molar yield of HMF with 97-98% of fructose conversion. The solvent was removed by the vacuum distillation to get dark brown viscous oil of crude HMF.

The Table 1 given below provides the HMF yields and fructose conversions with different acid catalyst using the process described above.

TABLE 1

| Example-1 | Catalyst | Time (Sec.) | Temperature (° C.) | % Fructose Conversion | % HMF Yield |
|---|---|---|---|---|---|
| A | PTSA | 120 | 120 | 98.78 | 92.12 |
| B | DIC$_4$T-1 | 120 | 120 | 98.52 | 85.76 |
| C | DIC$_4$T-2 | 120 | 120 | 97.45 | 84.00 |
| D | DIC$_4$T-3 | 120 | 120 | 97.60 | 93.85 |

Example 2

The experiment is carried out in batch mode operation under microwave heating at a frequency of 2.45 GHz. 1 gm of crystalline fructose was added to 8 ml solvent (as provided in Table 2) in a 20 ml sealed glass tube with magnetic stirrer; and stirred for 5 minute at room temperature to obtain a reaction suspension. 0.1 gm/cc of acid catalyst (PTSA) was added to this reaction suspension under continuous stirring. The resulting reaction mass was heated under stirring for 120 seconds by subjecting to microwave radiation. After 120 seconds, the reaction mixture was cooled to room temperature. The HPLC analysis of the sample was obtained which demonstrates 76-88% molar yield of HMF with 80-99% of fructose conversion. The solvent was removed by the vacuum distilled to get dark brown viscous oil of crude HMF.

The Table 2 given below provides the HMF yields and fructose conversions with different solvent using the process described above.

TABLE 2

| Example-2 | Solvent | Temperature (° C.) | Time (seconds) | % Fructose Conversion | % HMF Yield |
|---|---|---|---|---|---|
| A | IPA (iso-propyl alcohol) | 120 | 120 | 97.60 | 76.34 |
| B | TBA (tert-butyl alcohol) | 120 | 120 | 97.80 | 38.28 |
| C | NBA (n-butyl alcohol) | 120 | 120 | 80.22 | 46.81 |
| D | IAA (iso-amyl alcohol) | 120 | 120 | 94.66 | 16.90 |
| E | DMSO (dimethyl sulfoxide) | 120 | 120 | 98.94 | 88.14 |
| F | DMF (N,N-dimethyl formamide) | 120 | 120 | 99.18 | 88.70 |

Example 3

The experiment is carried out in batch mode operation under microwave heating at a frequency of 2.45 GHz. 1 gm of crystalline fructose was added to 8 ml isopropyl alcohol in a 20 ml sealed glass tube with magnetic stirrer; and stirred for 5 minute at room temperature. To this reaction suspension desired amount of PTSA (as provided in Table 3) was charged under stirring. The resulting reaction mass was heated for 90 seconds by subjecting to microwave radiation. After 90 seconds, reaction mass was cooled at room temperature. The HPLC analysis of the sample was obtained which demonstrates 74-88% molar yield of HMF with 94-98% of fructose conversion. The solvent was removed by the vacuum distilled to get dark brown viscous oil of crude HMF.

The Table 3 given below provides the HMF yields and fructose conversions with varying acid catalyst concentrations using the process described above.

TABLE 3

| Example-3 | Catalyst concentration (g/cc) | Time (Sec.) | Temperature (° C.) | % Fructose Conversion | % HMF Yield |
|---|---|---|---|---|---|
| A | 0.03 | 90 | 120 | 94.97 | 74.83 |
| B | 0.07 | 90 | 120 | 97.85 | 83.21 |
| C | 0.10 | 90 | 120 | 98.78 | 88.22 |
| D | 0.13 | 90 | 120 | 98.46 | 75.76 |

Example 4

The experiment is carried out in batch mode operation under microwave heating at a frequency of 2.45 GHz. 1 gm of crystalline fructose was added to 8 ml isopropyl alcohol in a 20 ml sealed glass tube with magnetic stirrer; and stirred for 5 minute at room temperature. To this reaction suspension 0.10 gm/cc of PTSA was charged under stirring.

The resulting reaction mass was heated to 120° C. by subjecting to microwave radiation for desired time period (as provided in Table 4). Thereafter the reaction mass was cooled to room temperature. The HPLC analysis of the sample was obtained which demonstrates the 32-91% molar yield of HMF and 50-100% of fructose conversion. The solvent was removed by the vacuum distilled to get dark brown viscous oil of crude HMF.

The Table 4 given below provides the HMF yields and fructose conversions with varying reaction time by using process described above.

TABLE 4

| Example-4 | Catalyst concentration (g/cc) | Time (Sec.) | Temperature (° C.) | % Fructose Conversion | % HMF Yield |
|---|---|---|---|---|---|
| A | 0.10 | 30 | 120 | 50.00 | 32.58 |
| B | 0.10 | 90 | 120 | 98.32 | 90.89 |
| C | 0.10 | 150 | 120 | 100.00 | 84.12 |
| D | 0.10 | 180 | 120 | 100.00 | 74.32 |

Example 5

The experiment is carried out in batch mode operation under microwave heating at a frequency of 2.45 GHz. 1 gm of crystalline fructose was added to 8 ml of solvent (as provided in Table 5) in a 20 ml sealed glass tube with magnetic stirrer; and stirred for 5 minute at room temperature. To this reaction suspension desired amount of acid catalyst ($DIC_AT-1$) was added under stirring. The resulting reaction mixture was heated for 120 seconds by subjecting to microwave radiation under stirring. After 120 seconds, the reaction mass was cooled at room temperature and catalyst was removed by vacuum filtration. The sample obtained demonstrated 50-94% molar yield of HMF with 80-99% of fructose conversion through HPLC analysis. The solvent was removed by the vacuum distilled to get dark brown viscous oil of crude HMF.

The Table 5 given below provides the HMF yields and fructose conversions with varying reaction solvent by using process described above.

TABLE 5

| Example-5 | Solvent | Temperature (° C.) | Time (seconds) | % Fructose Conversion | % HMF Yield |
|---|---|---|---|---|---|
| A | IPA | 130 | 120 | 97.60 | 93.85 |
| B | TBA | 130 | 120 | 97.80 | 50.23 |
| C | NBA | 130 | 120 | 80.22 | 59.30 |
| D | IAA | 130 | 120 | 94.66 | 52.34 |
| E | DMSO | 130 | 120 | 98.94 | 90.08 |
| F | DMF | 130 | 120 | 99.18 | 86.70 |

Example 6

The experiment is carried out in batch mode operation under microwave heating at a frequency of 2.45 GHz. 1 gm of crystalline fructose was added to 8 ml of solvent (as provided in Table 6) in a 20 ml sealed glass tube with magnetic stirrer; and stirred for 5 minute at room temperature. To this reaction suspension desired amount of acid catalyst ($DIC_AT-3$) was added under stirring. The resulting reaction mixture was heated for 120 seconds by subjecting to microwave radiation under stirring. After 120 seconds, the reaction mass was cooled at room temperature and catalyst was removed by vacuum filtration. The sample obtained demonstrated 50-94% molar yield of HMF with 80-99% of fructose conversion through HPLC analysis. The solvent was removed by the vacuum distilled to get dark brown viscous oil of crude HMF.

The Table 6 given below provides the HMF yields and fructose conversions with varying reaction solvent by using process described above.

TABLE 6

| Example-5 | Solvent | Temperature (° C.) | Time (seconds) | % Fructose Conversion | % HMF Yield |
|---|---|---|---|---|---|
| A | IPA | 130 | 120 | 97.60 | 93.85 |
| B | TBA | 130 | 120 | 97.80 | 50.23 |
| C | NBA | 130 | 120 | 80.22 | 59.30 |
| D | IAA | 130 | 120 | 94.66 | 52.34 |
| E | DMSO | 130 | 120 | 98.94 | 90.08 |
| F | DMF | 130 | 120 | 99.18 | 86.70 |

Example 7

The experiment is carried out in batch mode operation under microwave heating at a frequency of 2.45 GHz. 1 gm of crystalline fructose was added to 8 ml of solvent (as provided in Table 6) in a 20 ml sealed glass tube with magnetic stirrer; and stirred for 5 minute at room temperature. To this reaction suspension desired amount of acid catalyst ($DIC_AT-3$) was charged (as provided in Table 6). The resulting reaction mass was heated for 120 seconds by subjecting to microwave radiation under stirring. After 120 seconds, the reaction mass was cooled at room temperature and catalyst was removed by vacuum filtration. HPLC analysis of the sample demonstrated 61-93% molar yield of HMF with 97-100% fructose conversion. The solvent was removed by the vacuum distilled to get dark brown viscous oil of crude HMF.

The Table 7 given below provides the HMF yields and fructose conversions with varying catalyst $DIC_AT-3$ concentration by using process described above.

TABLE 7

| Example-6 | Catalyst Conc. (gm/cc) | Temperature (° C.) | Time (seconds) | % Fructose Conversion | % HMF Yield |
|---|---|---|---|---|---|
| A | 0.04 | 130 | 120 | 96.92 | 61.18 |
| B | 0.08 | 130 | 120 | 98.60 | 85.03 |
| C | 0.11 | 130 | 120 | 97.60 | 93.85 |
| D | 0.15 | 130 | 120 | 100.00 | 85.65 |

Example 8

The experiment is carried out in batch mode operation under microwave heating at a frequency of 2.45 GHz. 1 gm of crystalline fructose was added to 8 ml of isopropyl alcohol in a 20 ml sealed glass tube with magnetic stirrer; and stirred for 5 minute at room temperature. To this reaction suspension 0.11 gm/cc of acid catalyst ($DIC_AT$-3) was charged under stirring. The resulting reaction mass was heated under continuous stirring to 130° C. by subjecting to microwave radiation for desired time period (as provided in Table 8). After completion of the reaction, the reaction mass was cooled at room temperature and catalyst was removed by vacuum filtration. The sample obtained demonstrated 50-92% molar yield of HMF with 98-100% fructose conversion through HPLC analysis. The solvent was removed by the vacuum distilled to get dark brown viscous oil of crude HMF.

The Table 8 given below provides the HMF yields and fructose conversions with varying reaction time.

TABLE 8

| Example-7 | Catalyst concentration (g/cc) | Time (Sec.) | Temperature (° C.) | % Fructose Conversion | % HMF Yield |
|---|---|---|---|---|---|
| A | 0.10 | 30 | 130 | 97.61 | 50.01 |
| B | 0.10 | 90 | 130 | 98.52 | 73.16 |
| C | 0.10 | 120 | 130 | 99.12 | 92.22 |
| D | 0.10 | 180 | 130 | 100.00 | 74.32 |

Example 9

The experiment is carried out in batch mode operation under microwave heating at a frequency of 2.45 GHz. 1 gm of crystalline fructose was added to 8 ml of isopropyl alcohol in a 20 ml sealed glass tube with magnetic stirrer; and stirred for 5 minute at room temperature. To this reaction suspension 0.11 gm/cc of acid catalyst ($DIC_AT$-3) was charged under stirring. The resulting reaction mass was heated under continuous stirring to desired temperature (as provided in Table 9) by subjecting to microwave radiation for 120 seconds. After completion of the reaction, the reaction mass was cooled at room temperature and catalyst was removed by vacuum filtration. The sample obtained demonstrated 21-93% molar yield of HMF with 73-100% of fructose conversion through HPLC analysis. The solvent was removed by the vacuum distilled to get dark brown viscous oil of crude HMF.

The Table 9 given below provides the HMF yields and fructose conversions with varying reaction temperature by using process described above.

TABLE 9

| Example-8 | Catalyst concentration (g/cc) | Time (Sec.) | Temperature (° C.) | % Fructose Conversion | % HMF Yield |
|---|---|---|---|---|---|
| A | 0.11 | 120 | 100 | 73.14 | 21.98 |
| B | 0.11 | 120 | 120 | 98.16 | 74.60 |
| C | 0.11 | 120 | 130 | 98.27 | 93.22 |
| D | 0.11 | 120 | 150 | 100.00 | 80.27 |
| E | 0.11 | 120 | 180 | 100.00 | 72.76 |

Example 10

The experiment is carried out in batch mode operation under microwave heating at a frequency of 2.45 GHz. A desired amount of crystalline fructose (as shown in Table 10) was added to a requisite amount of the solvent in a 20 ml sealed glass tube with magnetic stirrer; and stirred for 5 minute at room temperature. To this reaction suspension 0.11 gm/cc of acid catalyst ($DIC_AT$-3) was charged under stirring. The resulting reaction mass was heated under continuous stirring to a temperature of 130° C. by subjecting to microwave radiation for 120 seconds. After completion of the reaction, the reaction mass was cooled at room temperature and catalyst was removed by vacuum filtration. The sample obtained demonstrated 26-92% molar yield HMF of with 99-100% fructose conversion through HPLC analysis. The solvent was removed by the vacuum distilled to get dark brown viscous oil of crude HMF.

The Table 10 given below provides the HMF yields and fructose conversions with varying fructose concentration by using process described above.

TABLE 10

| Example-9 | Fructose Conc. (gm/cc) | Temperature (° C.) | Time (seconds) | % Fructose Conversion | % HMF Yield |
|---|---|---|---|---|---|
| A | 0.125 | 130 | 120 | 99.340 | 52.34 |
| B | 0.063 | 130 | 120 | 98.520 | 92.83 |
| C | 0.031 | 130 | 120 | 100.000 | 54.23 |
| D | 0.016 | 130 | 120 | 100.000 | 26.23 |

Example 11

The experiment is carried out in batch mode operation under microwave heating at a frequency of 2.45 GHz. 1 gm of desired substrate (as shown in Table 1.1) was added to a requisite amount of the solvent (16 ml) in a 20 ml sealed glass tube with magnetic stirrer; and stirred for 5 minute at room temperature. To this reaction suspension 0.11 gm/cc of acid catalyst ($DIC_AT$-3) was charged under stirring. The resulting reaction mass was heated under continuous stirring to a temperature of 130° C. by subjecting to microwave radiation for 120 seconds. After completion of the reaction the reaction mass was cooled at room temperature and catalyst was removed by vacuum filtration. The sample obtained demonstrated 48-93% molar yield of HMF with 99-100% of fructose conversion through HPLC analysis. The solvent was removed by the vacuum distilled to get dark brown viscous oil of crude HMF.

The Table II given below provides the HMF yields and fructose conversions with varying substrate by using process described above.

TABLE 11

| Example-10 | Substrate | Temperature (° C.) | % Conversion | % Yield |
|---|---|---|---|---|
| A | Fructose | 130 | 97.60 | 93.85 |
| B | Glucose | 130 | 96.93 | 48.04 |
| C | Glucose/Fructose (1:1) | 130 | 97.65 | 60.78 |
| D | Sucrose | 130 | 100.00 | 86.84 |

Example 12

The experiment is carried out in batch mode operation under microwave heating at a frequency of 2.45 GHz. 1 gm of fructose was added to a requisite amount of the solvent (16 ml) in a 20 ml sealed glass tube with magnetic stirrer; and stirred for 5 minute at room temperature. To this reaction suspension 0.11 gm/cc of acid catalyst ($DIC_AT$-1) was charged under stirring. The resulting reaction mass was heated under continuous stirring to a temperature of 130° C. by subjecting to microwave radiation for 120 seconds. After completion of the reaction, the reaction mass was cooled at room temperature and catalyst was removed by vacuum filtration and the catalyst was recycled for subsequent runs (as provided in Table 12). The obtained filtrate sample was analyzed for HPLC which demonstrates 94-95% molar yield of HMF with 98-99% of fructose conversion. The solvent was removed by the vacuum distilled to get dark brown viscous oil of crude HMF.

The Table 12 given below provides the HMF yields and fructose conversions with number of catalyst recycle by using process described above.

TABLE 12

| Example-11 | Catalyst Run | Fructose Conc. | Temperature (° C.) | % Conversion | % Yield |
|---|---|---|---|---|---|
| A | 1 | 0.063 | 130 | 99.14 | 95.90 |
| B | 2 | 0.063 | 130 | 98.47 | 95.05 |
| C | 3 | 0.063 | 130 | 99.08 | 94.00 |
| D | 4 | 0.063 | 130 | 99.26 | 94.95 |
| E | 5 | 0.063 | 130 | 99.20 | 95.57 |

Example 13

The experiments was carried out in batch mode operation under conventional heating in a 300 ml Parr pressure reactor autoclave assembly having four peach bladed ampler and PID temperature controller with accuracy ±1° C. The autoclave was loaded with 2 gm of crystalline fructose in desired amount of solvent (32 ml) and a desired acid catalyst $DIC_AT$ (as provided in Table 13). The reaction mass in the autoclave was stirred for 5 minute at room temperature followed by nitrogen purging 2-3 times. The autoclave was pressurized to 15 kg/cm$^3$ using nitrogen and reaction mass was heated for 120 min under constant stirring. After 120 min of reaction, the reaction mass was cooled to room temperature and finally the nitrogen pressure was released. Heterogeneous catalyst in the reaction mass was removed by vacuum filtration. The sample from this filtrate was analyzed for HPLC and demonstrated 68-90% molar yield of HMF, with 96-98% fructose conversion. The solvent was removed by the vacuum distillation to obtain a dark brown viscous oil of crude HMF.

The Table 13 given below provides the HMF yields and fructose conversions with varying acid catalyst by using process described above.

TABLE 13

| Example-12 | Catalyst | Time (min) | Temperature (° C.) | % Fructose Conversion | % HMF Yield |
|---|---|---|---|---|---|
| A | PTSA | 120 | 120 | 96.51 | 68.54 |
| B | DICAT-1 | 120 | 120 | 98.52 | 70.97 |
| C | DICAT-2 | 120 | 120 | 98.12 | 70.36 |
| D | DICAT-3 | 120 | 130 | 98.32 | 90.76 |

Example 14

All the experiments were carried out in batch mode operation under conventional heating in a 300 ml Parr pressure reactor autoclave assembly having four peach bleded ampler and PID temperature controller with accuracy ±1° C. The autoclave was loaded with 2 gm of crystalline fructose in desired amount of solvent (32 ml) and a desired acid catalyst $DIC_AT$-3. The reaction mass in the autoclave was stirred for 5 minute at room temperature followed by 2-3 time nitrogen purging. The desired pressure (as provided in Table 14) was obtained by employing nitrogen gas and reaction mass was heated for 120 min under stirring followed by sample removal at desired time intervals. After 120 min reaction mass was cooled at room temperature, and nitrogen pressure was released. The heterogeneous catalyst was removed by vacuum filtration. The sample from this filtrate was analyzed through HPLC and depicted 40-90% molar yield of HMF, with 60-100% fructose conversion. Then the solvent was removed by the vacuum distilled to dark brown viscous oil of crude HMF.

The Table 14 given below provides the HMF yields and fructose conversions with varying pressure by using process described above.

TABLE 14

| Example-13 | Pressure (Kg/cm$^3$) | Time (min) | Temperature (° C.) | % Fructose Conversion | % HMF Yield |
|---|---|---|---|---|---|
| A | 5 | 120 | 120 | 60.51 | 40.54 |
| B | 10 | 120 | 120 | 78.52 | 52.97 |
| C | 15 | 120 | 120 | 98.32 | 90.76 |
| D | 20 | 120 | 120 | 99.32 | 84.76 |
| E | 25 | 120 | 120 | 100.00 | 60.40 |

Example 15

All the experiments were carried out in batch mode operation under conventional heating in a 300 ml Parr pressure reactor autoclave assembly having four peach bleded ampler and PID temperature controller with accuracy ±1° C. The autoclave was loaded with 2 gm of crystalline fructose in desired amount of IPA (32 ml) and a desired acid catalyst $DIC_AT$-3. The reaction mass in the autoclave was stirred for 5 minute at room temperature followed by 2-3 time nitrogen purging. The desired nitrogen pressure of 15 kg/cm$^3$ was employed and reaction mass was heated for desire time (as provided in Table 15) under constant stirring. After completion of reaction, reaction mass was cooled at room temperature and the nitrogen pressure was released. The heterogeneous catalyst was removed from the reaction mass by vacuum filtration. The sample from this filtrate was analyzed for HPLC and showed 30-90% molar yield of HMF, with 60-100% fructose conversion. The solvent was removed by the vacuum distillation to obtain dark brown viscous oil of crude HMF.

The Table 15 given below provides the HMF yields and fructose conversions with varying time period by using process described above.

TABLE 15

| Example-14 | Pressure (Kg/cm$^3$) | Time (min) | Temperature (° C.) | % Fructose Conversion | % HMF Yield |
|---|---|---|---|---|---|
| A | 15 | 30 | 120 | 60.51 | 30.54 |
| B | 15 | 90 | 120 | 78.52 | 52.97 |
| C | 15 | 120 | 120 | 98.32 | 90.76 |
| D | 15 | 180 | 120 | 99.32 | 70.72 |
| E | 15 | 240 | 120 | 100.00 | 62.42 |

Example 16

The heterogeneous solid acid catalyst $DIC_AT$ was prepared by sulfonic acid anchoring on aliphatic hydroxy groups of hydrophilic polymer through organic linkage. The typical experimental process for preparation of $DIC_AT$ is as follows:

The reaction was carried out in a four necked 250 ml dry round bottomed flask with heating oil bath, reflux condenser, thermometer pocket, addition funnel and over head stirrer. 1 gm of hydroxy polymer, (polyvinyl alcohol) was added under nitrogen blanketing. 10 ml of ethylene dichloride was charged in flask under slow stirring. The 9.5 ml of sulfonating agent, (chlorosulfonic acid) was added drop wise for 30 min through addition funnel under vigorous stirring. After the completion of addition reaction, reaction mass was stirred vigorously for 20-30 min at room temperature and then heated to reflux for 1 hr. On completion of 1 hr reflux, reaction mass was allowed to cool at room temperature and subsequently to 0° C.; thereafter 10 ml of aqueous methanol was added slowly through addition funnel within 30 min and maintained at 0° C. under vigorous stirring for another 30 min. The resulting black solid was then filtered by suction pump and washed by cold water till removal of chlorine from filtrate which was tested by $AgNO_3$ precipitation test. Finally the solid cake was suck dried by suction pump and kept for drying at 70-80° C. under vacuum. Resulting black color dry powder of $DIC_AT$ obtained was used for reaction.

Example 17

The synthesis of HMF in packed bed reactor was performed in steel column of 2×20 cm height with heating jacket having inlet outlet temperature sensor and pressure control valve. The 5 cm catalyst bed was packed with sufficient amount of inert material. Before passing the substrate through packed bed column, the column was pre equilibrated by passing 2-5 column volume (CV) of fresh water and IPA to obtain column temperature of 120° C. and 10-15 kg/cm³ pressure. The pre heated 100 ml 6.25% solution of fructose in IPA was passed through catalyst bed maintained at 120° C. by conventional heating with desire flow rate in cyclic loop by means of binary piston pressure pump. Simultaneously, the samples from reaction mixture were removed at different time intervals for in process HPLC analysis. Once the requisite HMF yield and fructose conversion were obtained, the substrate flow was stopped and catalyst bed was washed by 2 CV of fresh IPA to remove the line and the catalyst bed hold up. The resulting composite fraction was analyzed through HPLC and depicted results in the range of 88-94% HMF yield with 95-100% of fructose conversion.

Example 18

The synthesis of HMF in packed bed reactor was performed in steel column of 2×20 cm height with heating jacket having inlet outlet temperature sensor and pressure control valve. The 5 cm catalyst bed was packed with sufficient amount of inert material. Before passing the substrate through packed bed column, the column was pre equilibrated by passing 2-5 column volume (CV) of fresh water and IPA to obtain column temperature of 120° C. and 10-15 kg/cm³ pressure. The pre heated 100 ml 6.25% solution of fructose in IPA was passed through catalyst bed maintained at 120° C. by microwave heating with desired flow rate in cyclic loop by means of binary piston pressure pump. Simultaneously, the samples from reaction mixture were removed at different time intervals for in process HPLC analysis. Once the requisite HMF yield and fructose conversion were obtained, the substrate flow was stopped and catalyst bed was washed by 2 CV of fresh IPA to remove the line and the catalyst bed hold up. The resulting composite fraction was analyzed through HPLC and depicted results in the range of 88-94% HMF yield with 95-100% of fructose conversion.

Advantages Gained in the Example Illustrative Process in This Subject Matter:

The present disclosure relates to a process of preparing 5-hydroxymethyl furfural (5-HMF) from saccharides utilizing an acid catalyst. The acid catalyzed cyclodehydration process for synthesis of 5-HMF provides a simple and cost effective route for the production of 5-HMF in monophasic organic solvent. The heterogenous solid acid catalyst, $DIC_AT$ used in the process disclosed herein has excellent catalytic activity, stability, and selectivity towards desired product. Due to higher selectivity of catalyst, formation of side products such as polymers, humins, levulinic acid, and condensation products is significantly reduced. The overall process employs use of monophasic organic solvents (low boiling, or high boiling) which are easy to separate with minimum energy utilization for solvent distillation. The process is carried out in significantly decreased reaction time through conventional or microwave assisted heating resulting in increased productivity.

The comprises microwave assisted short time reaction that is carried out in a monophasic organic solvent at temperature ranges of 100-180° C., thus providing process feasibility at an economical cost and with low energy consumption. The short reaction time of 30-120 seconds enhance the bulk production and economics of 5-HMF production in the given time period.

The present process for synthesis of 5-HMF synthesis involves lower energy utilization with production of minimum waste and effluents.

The disclosed process is therefore a green and efficient process which results in higher selectivity and yield; has a higher conversion rate with enhanced catalytic stability, has ease of separation and most importantly has the advantage of recycling the catalyst with 100% recovery.

Although the subject matter has been described in considerable detail with reference to certain examples and implementations thereof, other implementations are possible. As such, the spirit and scope of the appended claims should not be limited to the description of the preferred examples and implementations contained therein.

What is claimed is:

1. A process for preparing a furan derivative, the process comprising the steps of:
   a) contacting a sugar with a monophasic organic solvent to obtain a reaction mixture; and
   b) subjecting the reaction mixture to a temperature in the range from 100° C. to 180° C., in presence of an acid catalyst, for a time period in the range of about 0.5 min to about 2.0 h to obtain at least 70% conversion of the sugar to a single furan derivative,
   wherein the acid catalyst is a heterogeneous solid acid catalyst, wherein the heterogeneous solid acid catalyst is a hydrophilic sulfonated solid porous matrix.

2. The process as claimed in claim 1, wherein the sugar is selected from the group consisting of glucose, fructose, sucrose, and combinations thereof.

3. The process as claimed in claim 1, wherein the monophasic organic solvent comprises $C_1$ to $C_{15}$ alcohols.

4. The process as claimed in claim 1, wherein the acid catalyst is used in an amount in the range of 0.01 to 5 g/cc of the reaction mixture.

5. The process as claimed in claim 1, wherein the furan derivative is obtained by at least one of a microwave assisted heating method or a conventional heating method.

6. The process as claimed in claim 1, wherein the furan derivative is 5-hydroxymethyl furfural (5-HMF).

7. The process as claimed in claim 1, wherein the sugar is fructose.

8. The process as claimed in claim 1, wherein the monophasic organic solvent comprises $C_1$ to $C_4$ alcohols selected from the group consisting of methanol, ethanol, n-propanol, iso-propanol, sec-butanol, tert-butanol, and combinations thereof.

9. The process as claimed in claim 1, wherein the monophasic organic solvent is iso-propanol.

10. The process as claimed in claim 1, wherein the acid catalyst is used in an amount in the range of 0.1 to 1.0 g/cc.

* * * * *